United States Patent [19]

Sharp et al.

[11] Patent Number: 4,687,737
[45] Date of Patent: Aug. 18, 1987

[54] MAMMALIAN SUPPRESSOR GENES

[75] Inventors: Phillip A. Sharp, Newton, Mass.; Mario R. Capecchi, Salt Lake City, Utah; Uttam L. RajBhandary, Lexington, Mass.; Frank A. Laski, Southfield, Mich.

[73] Assignee: Massachusetts Institute of Technology, Cambridge, Mass.

[21] Appl. No.: 751,461

[22] Filed: Jul. 2, 1985

Related U.S. Application Data

[63] Continuation of Ser. No. 441,200, Nov. 12, 1982, abandoned.

[51] Int. Cl.[4] .................... C12N 15/00; C12N 5/00; C12N 5/02; C12N 7/00
[52] U.S. Cl. ...................................... 435/68; 435/70; 435/71; 435/91; 435/172.1; 435/172.3; 435/235; 435/239; 435/320; 435/240.2; 536/27; 424/89; 424/93
[58] Field of Search ................ 435/68, 70, 91, 172.3, 435/240, 241, 235, 239, 317, 172.1, 71; 536/27; 935/5, 70, 71; 424/89, 93

[56] References Cited

PUBLICATIONS

Müller et al., "Nucleotide Sequence of Genes Coding for tRNA$^{Phe}$ and tRNA$^{Tyr}$ from a Repeating Unit of X. Laevis DNA", Cell 19: 345, (1980).

Wallace et al., "Directed Deletion of a Yeast Transfer RNA Intervening Sequence", Science 209: 1396, (1980).
Hamer et al., "Expression of the Shromosomal Mouse Beta$^{mag}$-Globin Gene Cloned in SV40", Nature 281: 35, (1979).
Hamer, "SV40 Carrying an Escherichia Coli Suppressor Gene", in Recombinant Molecules: Impact on Science and Society, R. F. Beers, Jr. et al., (ed.), Raven Press, New York, 1977, pp. 317–335.
Hamer et al.: Chem. Abstr. 88:2962f, (1978), of Miles Int. Symp. Ser. 10, 317, (1977).
Laski et al.: Proc. Natl. Acad. Sci. U.S.A. 79, 5813, (1982).
Laski et al.: Nucleic Acids Res. 10, 4609, (1982).
Temple et al.: Nature 296, 537, (1982).
Hudziak et al.: Cell 31, 137, (1982).

Primary Examiner—James Martinell
Attorney, Agent, or Firm—James E. Maslow; Thomas J. Engellenner

[57] ABSTRACT

A method of suppressing a nonsense codon in a gene in a mammalian cell by preparing an oligonucleotide primer having a mismatched anticodon region corresponding to the nonsense codon; preparing a DNA template for production of a tRNA molecule enabling the insertion of an amino acid when the nonsense codon is translated; forming a suppressor gene from said template and primer by site specific mutagenesis; and transforming the suppressor gene into the cell.

21 Claims, 4 Drawing Figures

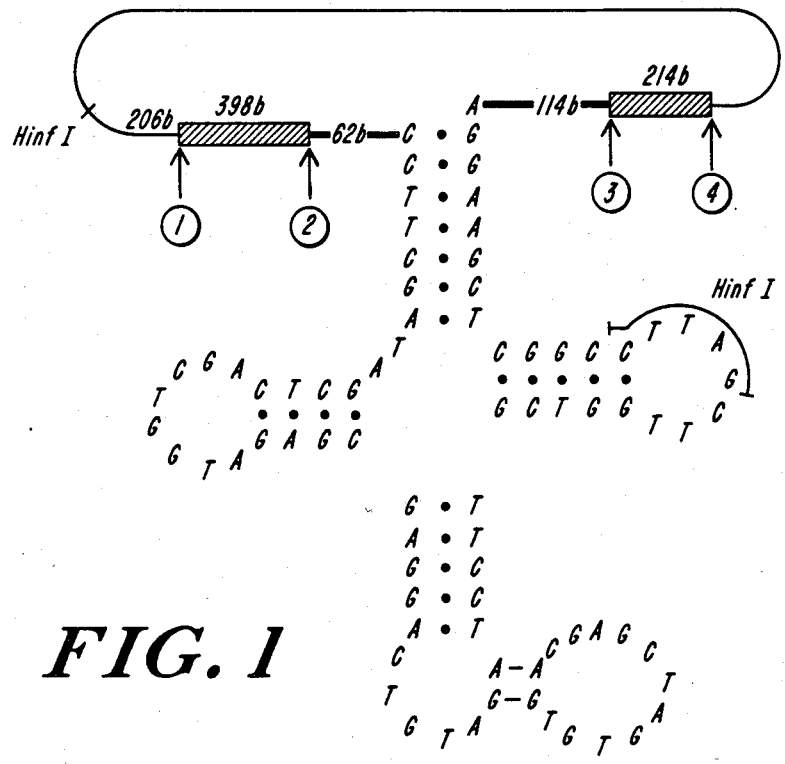
FIG. 1
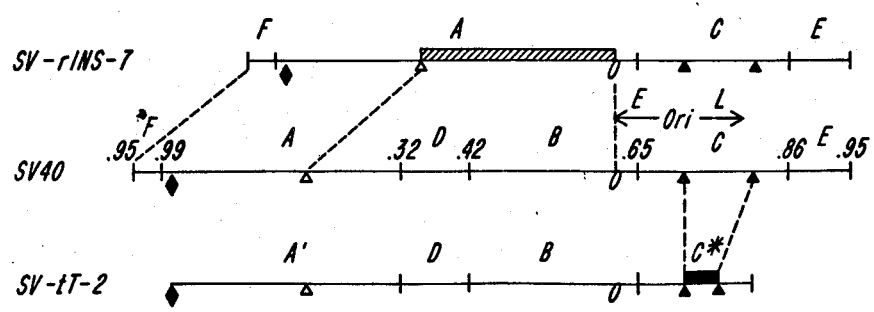
FIG. 2
FIG. 3

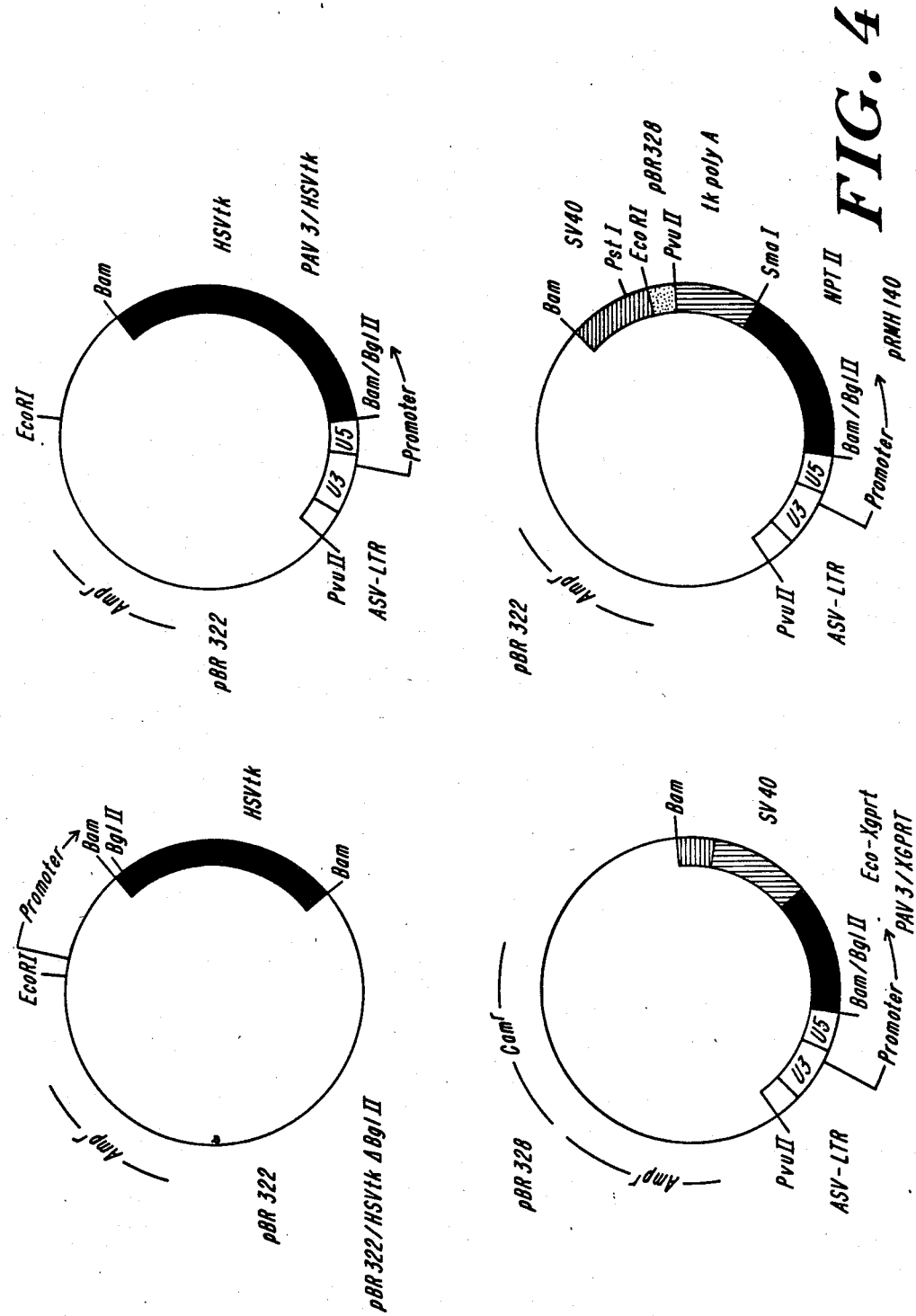

MAMMALIAN SUPPRESSOR GENES

The U.S. Government has rights in this invention pursuant to NSF Grant No. PCM 78-23230.

This application is a continuation of application Ser. No. 441,200 filed Nov. 12, 1982 now abandoned.

TECHNICAL FIELD

This invention relates to genetic engineering and, in particular, to suppressor genes for higher organisms.

BACKGROUND OF THE INVENTION

Attention is directed to an article by the inventors and a colleague, entitled "An Amber Suppressor tRNA Gene Derived By Site-Specific Mutagenesis: Cloning and Function in Mammalian Cells" in the *Proceedings of the National Academy of Science* Vol. 79, No. 19, pp. 5813-5817 (1982), and an article entitled "Establishment of Mammalian Cell Lines Containing Multiple Nonsense Mutations and Functional Suppressor tRNA Genes" in *Cell* Vol. 31, No. 1, pp. 137-146 (1982), both herein incorporated by reference.

Of the sixty-four possible codon triplets which form the genetic code, there are three nonsense codons which are known to stop protein production at cellular ribosomes; the other sixty-one triplets in the code correspond to one or another amino acid. When genetic instruction are translated at the ribosomes, the amino acids are strung together to form complex polypeptides. However, when a nonsense codon is read, it is interpreted as a stop signal terminating the protein production. The three nonsense codons are UAG (amber), UAA (ochre) and UGA (opal).

Nonsense codons are sometimes caused by mutations and, as a result, genetic phenotypes may not be expressed. Despite the presence of the gene directing expression, a crucial protein may not be produced because of an unwanted stop signal reaches a ribosome and terminates the unfinished protein. There are also times when one wants to manipulate a gene to include a nonsense codon. In either case, there exists a need for a suppression mechanism which would permit the cellular ribosomes to "read through" such stop signals when they are unwanted.

Suppressor genes for prokaryotic cells, such as *E. coli* bacteria, have been isolated and studied. See, for example, Goldberg, *Biological Regulation and Development* Vol. 1 *Gene Expression*, pp 433-475 (1979). Such suppressors operate by producing tRNA molecules which possess an altered anticodon for reading the nonsense codon as if it were a normal instruction. For example, an amber mutation results in the creation of a UAG codon in messenger RNA. An amber suppressor gene produces tRNA with a CUA anticodon, thereby inserting an amino acid at the UAG site and permitting continued translation.

While suppressor genes have been characterized for *E. coli* bacteria and similar work is being conducted on yeasts, the isolation of suppressor genes in mammalian cells has not been successful due to the complexity of such cells and the lack of adequate selection protocols. Moreover, the transformation of bacterial suppressor genes into mammalian cells has not been successful because of the nature of higher organism cells. We are not aware of any successfully synthesized suppressor genes for mammalian cells, other than the ones reported herein. Temple et al in an article entitled "Construction of a Functional Human Suppressor tRNA gene: an approach to gene therapy for Bthalassaemia" Vol. 296 *Nature* pp 537-542 (Apr., 1982) report the synthesis of a suppressor gene and its expression in frog eggs.

There exists a need for suppressor genes for mammalian cells. The availability of mammalian cell lines with well characterized tRNA suppressor mutants would greatly facilitate genetic analysis of nonsense mutants in mammalian cells and in particular animal viral genomes. Moreover, the availability of such cell lines should open new pathways for the use of mammalian host cells as growth media for vaccines and other valuable products.

SUMMARY OF THE INVENTION

We have discovered a method of suppressing nonsense codons in mammalian cells and have demonstrated the cloning, expression and function in vivo of a suppressor gene in mammalian cells. In particular, we have generated an amber suppressor tRNA gene from an X. laevis tyrosine gene by site specific mutagenesis using a mismatched oligonucleotide sequence as a primer. This tRNA gene is expressed and produces functional tRNA which suppresses amber mutations both in vivo and in vitro.

In transforming the suppressor gene into mammalian cells we used an SV40 vector, a small covalently closed circular DNA molecule, the nucleotide sequence of which has already been determined.

In vivo activity of the suppressor tRNA gene was first shown by the fact that preinfection of monkey cells (CV-1) cells with the SV40-tRNA suppressor recombinant efficiently suppressed the amber nonsense mutation in the 30,000 dalton fusion protein of both mutants of adenovirus 2-SV40 hybrid viruses.

We next isolated nonsense mutants in the Herpes simplex virus thymidine kinase gene (HSV-tk), the *E. coli* xanthine quanine phosphoribosyl gene (Ecogpt) and the aminoglycoside 3' phosphotransferase gene coded for by the Tn5 transposon (NPT-II). Each gene was engineered to be transcriptionally and translationally competent in both mammalian cells and *E. coli* and when introduced into either cell type each gene confers a selectable phenotype. Ecogpt and NPT-II were particularly useful genes for DNA-mediated gene transfer studies since they confer a dominant selectable phenotype in mammalian cells. The *E. coli* gpt gene had previously been cloned into an SV40 vector which allowed expression of this gene in mammalian cells. Further, since mammalian cells cannot ordinarily use xanthine as a purine source, a selection procedure is known in which cell survival depends on acquisition of a functional gpt gene. Expression of the Tn5 kanamycin resistance gene (NPT-II) in mammalian cells has been previously achieved by linking it to HSV-tk controlling sequences. Transfer of this gene into mammalian cells renders them resistant to the aminoglycoside G418 (a derivative of gentamycin).

The strategy which we employed was to obtain and characterize nonsense mutations in *E. coli* and then to transfer them into cultured mammalian cells. These multiply marked somatic cell lines were then available for isolation and maintenance of nonsense suppressor genes. In using this approach we have in effect coupled bacterial and somatic cell genetics. In the description which follows, we explain the synthesis of an amber (UAG) suppressor gene by site specific mutagenesis of a *Xenopus-laevis* tyrosine tRNA gene and how following cloning into SV40 DNA, this gene was shown to function as a suppressor in vivo by coinfecting monkey cells (CV-1) with amber mutants in Adenovirus 2-SV40 hybrid virus. Additionally we describe how we have microinjected this amber suppressor gene into mouse cells containing HSV-tk, Ecogpt and NPT-II amber mutants and applied one or more selections to isolate permanent cell lines containing functional suppressor tRNA genes.

One particular use for mammalian suppressor genes will be in producing attenuated live virus vaccines. In such production one can mutate the virus, against which a vaccine is sought, by incorporating into the genetic material of the virus at least one nonsense codon to disrupt viral replication. The mutated virus can then be grown in a host having a suppressor gene capable of suppressing the nonsense codon mutation and thus permitting viral replication. Finally the viruses are harvested and vaccine produced. The advantage of this technique is that the virus produced will be unable to replicate outside of the host environment absent the suppressor gene. Moreover, this technique potentially can greatly reduce the expense of vaccine production because the multiple steps of attenuating the viral potency by growth and regrowth under selective conditions would be avoided.

Our invention will next be described in connection with experimental results; however, it should be clear that various changes and modifications may be made to our techniques without departing from the spirit or scope of our claims. For example, while our invention is described in connection with suppressing nonsense codon mutations, our technique can also be used to suppress frameshift mutations. A frameshift mutation typically arises when a nucleotide is deleted from the gene by mutation, resulting in disruption of translation at the ribosomes because the nucleotide triplets no longer represent proper instructions; essentially, the codons read by ribosomes are out of synchronization with the original genetic instructions. Our invention can solve this problem by producing variants of tRNA that read for examples 2 or 4 nucleotides in sequence instead of the normal 3 nucleotide codon. In this fashion protein production at the ribosome is not disrupted and is returned to synchronization.

Various techniques may be employed to introduce the genes containing nonsense codons and frameshift mutations as well as suppressor genes into cells. For examples, transfection, microinjection or phage vectors may be employed. In particular applications introduction of the nonsense or frameshifted genes can occur simultaneously with the introduction of the suppressor gene or, in other applications, the operations can be conducted sequentially.

BRIEF DESCRIPTION OF THE FIGURES

FIG. 1 is a schematic diagram of the sequence of a suppressor tRNA gene.

FIG. 2 is a schematic diagram of a oligonucleotide primer used according to our invention to prepare a template for tRNA.

FIG. 3 is a schematic diagram of a technique for introducing a suppressor gene into a plasmid.

FIG. 4 is a schematic diagram of several plasmids used for generation of nonsense mutations.

DESCRIPTION OF THE PREFERRED EMBODIMENTS

The sequence of an $X.$ $laevis$ gene for tRNA$^{Tyr}$ is shown in FIG. 1. A 263 bp fragment containing this gene has previously been cloned into the late region of SV40 and its expression studied after infection of monkey cells. The $X.$ $laevis$ gene is efficiently transcribed and the tRNA is processed and modified. Thus, we concluded that this tRNA$^{Tyr}$ gene would be an excellent candidate for site-specific mutagenesis to generate an amber suppressor.

The basic scheme for site-specific mutagenesis involves the use of a single stranded circular DNA (M13-tT) carrying the $X.$ $laevis$ tRNA$^{Tyr}$ gene as a template for the synthesis of covalently closed circular duplex DNA in the presence of an oligonucleotide as primer.

M13-tT contained a 263 bp Hae II-Hha I fragment of X. laevis DNA flanked by SV40 DNA sequences cloned into the Hind III site of M13-mp5. The tRNA$^{Tyr}$ gene segment was subcloned from a recombinant pSV-tT into the M13-mp5 vector. M13-mp5 is a derivative of M13-mp2 that has a Hind III-Eco RI polylinker cloned into the M13-mp2 Eco RI site. As shown in FIG. 1 the descriptions of the recombination sites are as follows: (1) the Hind III site of SV40 (mu 0.65) was joined to the Hind III site of the M13-mp5 polylinker; (2) the Hha I site of $X.$ $laevis$ DNA was joined to the Hha I site of SV40 (mu 0.72); (3) the Hae II site of the $X.$ $laevis$ DNA was joined to the Hae II site of SV40 (mu 0.82); (4) the Hind III site of SV40 (mu 0.86) was joined to the Hind III site of the M13-mp5 polylinker. The sequence of the coding region of the mature tRNA$^{Tyr}$ gene and its intervening sequence as well as the Hinf I sites that immediately flank the anticodon region are shown in FIG. 1.

The 13 base long oligonucleotide primer CACC-TAGAGTCCT was synthesized using a modified phosphotriester method and purified as a single peak on HPLC. A 5' terminal phosphate was added with T4 polynucleotide kinase. As shown in FIG. 2, the primer used contained a mismatch in the anticodon region of the tRNA gene. To ensure specific priming by the oligonucleotide, the M13-tT DNA used was freed of DNA fragments by alkaline sucrose gradient centrifugation. Conditions for specific priming were established by using 5'-$^{32}$P-labeled oligonucleotide primer and analyzing the elongation product by gel electrophoresis following digestion with Hind III. As expected, more than 50% of radioactivity was observed in the small 873 bp Hind III fragment which contains the tRNA$^{Tyr}$ gene.

M13-tT virion DNA (9.0 μg) and the oligonucleotide primer (1.0 μg) were mixed in 11 μl of hybridization buffer (8 mM Tris pH 7.4, 20 mM NaCl, 4 mM MgCl$_2$, 0.4 mM β-mercaptoethanol). After one hour on ice, 5 μl of the DNA solution was added to 8 μl of 30 mM Tris, pH 7.4, 15 mM MgCl$_2$, 1.5 mM β-mercaptoethanol, 1.245 mM dNTP and 0.6 mM ATP. After 10' at 37° C., 2 μl of DNA polymerase I (Klenow fragment, New England Biolabs 1100 units/ml) and 1.5 μl of T4 ligase (New England Biolabs, 4×10$^5$ units/ml) were added. After 2 hours at 37° C. the reaction was loaded onto an agarose gel containing 0.6 μg/ml ethidium bromide.

The oligonucleotide primed product should contain both incomplete and complete duplex DNAs. Since incomplete duplex DNAs could contribute to high wild type (w.t.) background, covalently closed duplex DNAs were purified by electrophoresis in the agarose gel with ethidium bromide and then used to transfect $E.$ $coli.$ Forty independent phage plaques were screened for the desired site-specific mutation. Phage from each plaque was used to infect E. coli and RF DNAs were isolated from the infected cells and analyzed by digestion with Hinf I followed by electrophoresis on a 5% polyacrylamide gel. The desired site-specific mutation generates a new Hinf I site within the tRNA gene as shown in FIG. 1. Two clones containing the new Hinf I site were further analyzed and confirmed to possess the desired mutation by DNA sequencing. The desired mutation was clearly present in the mutant recombinant DNA. The same result was obtained from sequencing the other candidate M13tT mutant.

DNA segments from the M13 recombinants containing the tRNA genes were excised and cloned into the late region of SV40 DNA as shown in FIG. 3. Identical constructs were prepared with both the w.t. *X. laevis* tRNA gene and the tRNA (Su+) gene. M13-tT and M13-tT(Su+) were each cleaved with Kpn I (in the SV40 sequences at mu 0.72) and Eco RI (in the M13mp5 polylinker which is adjacent to the SV40 Hind III site at m.u. 0.86) and the DNA fragment containing the tRNA gene purified by gel electrophoresis. This fragment was cloned into a pBR322-SV40 recombinants (which were joined at their Bam HI sites) that had been cleaved with Kpn I (at SV40 m.u. 0.72) and Eco RI (at SV40 m.u. 1.0). This places the tRNA gene in the late region of SV40 in the same polarity as late mRNA transcription. The resulting clones were designated pSV-tT-2 and PSV-tT-2(Su+).

In FIG. 3 the solid lines represent the position of Hind III sites in SV40 and the map units of the sites are shown. SV-rINS-7 has an insertion of sequences from a rat preproinsulin gene and a deletion of sequences from the early region of SV40 creating the new restriction fragment A*. SV-tT-2 has an insertion-deletion in the late region of SV40 creating the new restriction fragment C* and a deletion of late SV40 sequences (mu 0.86 to 1.0) creating the new restriction fragment A'. The origin of replication (ori) and the direction of early and late transcription are shown. Restriction sites used in construction of the recombinant: : HhaI site; Δ: Bcl I site; o: Tag I site; : Eco RI site.

Virus stocks of the SV40 recombinants were prepared by co-transfection of CV-1 cells with a SV40 rat preproinsulin recombinant, SV-rINS-7, that has a deletionsubstitution in the early gene region of SV40. Both complementing DNAs were excised from pBR322 sequences by digestion with the appropriate restriction endonculeases, circularized by ligase and transfected on CV-1 cells using DEAE dextran. Approximately one week after co-transfection, the CV-1 cells underwent a cytopathic degeneration. The resulting virus stocks were harvested and labeled SV-tT-2/SV-rINS-7 and SV-tT-2(Su+)/SV-rINS-7.

Amplification of the amber suppressor gene in CV-1 cells did not interfere with SV40 reproduction. A 10 cm plate of CV-1 cells infected with 0.1 ml of either SV-tT-2/SV-rINS-7 or SV-tT-2(Su+)/SV-rINS-7 virus yielded comparable amounts of viral DNA 48 hrs p.i. Digestion of the $^{32}$P-labeled DNA with Hind III revealed that each stock contained the two complementing DNAs with no detectable contaminating w.t. SV40 DNA or variant DNA. In addition, the amount of labeled viral DNA extracted from recombinant infected cells was comparable to that found 48 hrs post infection with 10 m.o.i. of SV40. Thus, both the w.t. tRNA$^{Tyr}$ and the amber suppressor tRNA$^{Tyr}$ SV40 recombinants gave good virus stocks.

Expression of the tRNA$^{Tyr}$ (Su+) gene in monkey cells was examined by labeling SV-tT-2 (Su+)/Sv-rINS-7 infected cells with $^{32}$PO$_4$ from 46 to 52 hours post infection and analyzing total RNA for overproduced tRNAs. Cells infected with an equal volume of SV-tT-2/SV-rINS-7 were analyzed in parallel. In both cases, the $^{32}$P-labeled RNA was resolved by electrophoresis in a 7.5% acrylamide -8.3M urea gel. W.t. tRNA$^{Tyr}$ gene was efficiently expressed yielding a prominent band migrating as expected for a 76 nucleotide long tRNA and tRNA$^{Tyr}$(Su+) gene was expressed at about 1/5 level of the w.t. gene but again yielding a prominent band migrating as expected for a 76 nucleotide long tRNA. T1 fingerprint analysis of this tRNA showed that it contained the amber Su+ anticodon. The reduced level of the tRNA$^{Tyr}$ from the Su+ mutant was most likely due to inefficient splicing. In spite of this, infected cells still accumulate sufficient amounts of suppressor tRNA to efficiently suppress amber mutations if the tRNA is active in protein translation.

In vivo suppression of amber nonsense codons was first demonstrated using nonsense mutations of an adenovirus 2-SV40 hybrid virus (Ad2+ND1). The hybrid virus Ad2+ND1 codes for a 30,000 fusion protein which is specified by both adenovirus and SV40 sequences, specifically the C-terminal sequence of the SV40 large T antigen. The presence of this region of the SV40 large T antigen gene allows Ad2+ND1 to grow in monkey cells. The Ad2+ND1 mutants are defective for synthesis in vivo of the 30,000 dalton protein but stimulate synthesis of shorter proteins. Two of the Ad2+ND1 mutants, 140 and 162, where identified as amber mutants as addition of a yeast amber tRNA$^{Ser}$ suppressor in an in vitro translation reaction permitted synthesis of the 30,000 fusion protein. One of the Ad2+ND1 mutants, 71, was identified as an ochre mutant as in vitro translation of the 30,000 dalton fusion protein was dependent on addition of a yeast ochre tRNA$^{Ser}$ suppressor. These mutants then provide a convenient means of testing the in vivo suppression activity of the *X. laevis* tRNA$^{Tyr}$ (Su+).

CV-1 cells were infected with either SV40, SV-tT-2/SVrINS-7, or SV-tT-2 (Su+)SV-rINS-7 and incubated at 37° C. for 24 hours to permit synthesis of viral encoded products, including tRNAs. These cultures were then infected with either Ad2+ND1, Ad2+ND1 71, Ad2+ND1 140 or Ad2+ND1 162 at approximately 50 m.o.i. Twenty-four hours postinfection with the hybrid viruses, the cells were labeled by addition of $^{35}$S methionine and incubated for one more hour. Total cell extracts were prepared from each $^{35}$S-labeled culture and SV40 large T antigen related proteins were immunoprecipitated by addition of a monoclonal antibody. This antibody binds to amino acid sequences in the carboxyl terminus of T and immunoprecipitates the 30,000 fusion protein. The 30,000 fusion protein was immunoprecipitated from cells infected with Ad2+ND1 but not from CV-1 cells infected with either of the Ad2+ND1 mutants nor from CV-1 cells that were pre-infected with the SV40-*X. laevis* tRNA$^{Tyr}$ recombinant (SV-tT-2/SV-rINS-7) and then infected with either Ad2+ND1 mutant. However, the amber nonsense mutants Ad2+ND1 140 and 162 were suppressed in CV-1 cells preinfected with the SV40 tRNA-$^{Tyr}$ (Su+) recombinant (SV-tT-2 (Su+)/SV=rINS-7). That the suppression was quite efficient is indicated by the fact that the amount of 30,000 dalton protein synthesized was equivalent to that found after Ad2+ND1 infection, suggesting full suppression. Suppression by the *X. laevis* tRNA$^{Tyr}$(Su+) gene was specific for amber mutations since synthesis of the 30,000 dalton fusion protein was not observed following infection with the ochre mutant, Ad2+ND1 71, into CV-1 cells preinfected with SV-tT-2 (Su+)/SV-rINS-7 virus. We concluded that expression of the *X. laevis* tRNA (Su+) gene in mammalian cells generates a permissive state for synthesis of proteins coded by messenger RNAs containing amber nonsense mutations.

In our next demonstration of suppressor gene activity in mammalian cells plasmids capable of expressing Ecogpt and NPT-II respectively in both *E. coli* and mammalian cells were prepared by placing the coding sequence of these genes under the control of the avian sarcoma virus (ASV) LTR promoter (see FIG. 4 for the plasmid constructions). It had previously been shown by others that sequences in ASV-LTR functions as a promoter in bacteria and could substitute for the normal bacterial tetracycline and neomycin resistance promoters. The above Ecogpt and NPT-II plasmid DNAs efficiently transformed appropriate *E. coli* mutant strains to yield respectively gpt+ and kanamycin-resistant colonies. The HSV-tk coding sequence when placed down stream of the ASV-LTR also functioned in *E. coli* but not sufficiently well to permit easy isolation of suppressible nonsense mutations, thus a two step procedure was adopted. The HSVtk coding sequence was first placed under the control of the tetracycline resistance gene of pBR322 for expression in *E. coli*. Following the isolation and characterization of the HSV-tk nonsense mutations in *E. coli*, the HSV-tk coding sequences were placed under the control of the retrovirus ASV-LTR promoter for expression in mammalian cells.

An added advantage of the ASV-LTR promoter for these experiments was its strength in mammalian cells. Use of the ASV-LTR promoter to initiate transcription of the HSV-tk coding sequences (BglII to BamHI) consistently yielded 10-fold more ASV-LTR-HSV-tk hybrid mRNAs than normal HSV-tk transcripts using the authentic HSV-tk promoter.

With reference to FIG. 4, pBR322/HSV-tk ΔBgl II was derived from a derivative of pBR322/HSV-tk that contains two Bgl II restriction sites in the 3.4 kb HSV-tk Bam HI fragment approximately 100 and 600 base pairs from the 5'-Bam HI site. Cleavage of this plasmid DNA with Bgl II followed by religation removes the HSV-tk promoter and places the HSV-tk coding sequence under the control of the PBR322 tetracycline promoter. In the plasmids PAV3/HSV-tk, PAV3/gpt and pRMH140 the HSV-tk, Ecogpt and NPT-II coding sequences are under the control of sequences in the avian sarcoma virus LTR. The fusion of the virus LTR with the respective coding sequence occurs at the LTR Bst EII site which was converted to a Bam HI site. The plasmid DNAs then were mutagenized in vitro with hydroxylamine and transfected into the appropriate *E. coli* strain. Ecogpt− mutants were selected directly on 6-thioguanine plates. HSV-tk− and NPT-II− mutants were identified by first isolating the bacterial transformants on ampicillin plates, followed by screening the mutants by replica plating to selective and nonselective plates and scoring for the loss of tk or NPT-II activity. Among the collection of null mutants, nonsense mutants were identified by their suppressibility with specialized transducing phages containing amber (UAG) or ochre (UAA) suppressor genes. HSV-tk−, Ecogpt− or NPT− mutants were plated on agar containing the appropriate selective medium. A drop of a phage lysate carrying an amber suppressor gene was placed on each plate. Growth occurred only where the phage carrying the nonsense suppressor gene was added. Using this procedure a series of amber and ochre mutants varying in their ability to be suppressed by the different transducing phages where identified. For all of the subsequent experiments we selected a single amber mutant in each gene on the basis of its ability to be efficiently suppressed by a tyrosine inserting amber suppressor (SuIII). These mutants are designated as PAV-3/HSV-tk−am1142, PAV-3/Ecogpt−am63 and PAV-3/NPT-IIam28. These three amber mutant genes were comicroinjected into LMtk−/APRT/HGPRT− cells with a selectable marker gene and cell lines established. Such cell lines were shown to contain the amber mutant genes by microinjection of yeast suppressor tRNA. Microinjection of amber suppressor tRNA but not ochre or wild type tRNA restored tk and gpt enzymatic activity to these cells. The presence of tk and gpt enzymatic activity in the cells receiving an injection of tRNA was determined 24 hours after injection by following the incorporation of $^3$H-thymidine, $^3$H-guanine or $^{14}$C-xanthine into nucleic acid by autoradiography. Since mammalian cells can not utilize xanthine as a purine source, incorporation of $^{14}$C-xanthine allowed detection of Ecogpt enzymatic activity in the presence of cellular HGPRT activity. Guanine and xanthine were incorporated into both DNA and RNA explaining the cytoplasmic and nuclear labelling pattern.

A cell line containing HSV-tk− (amber), Ecogpt− (amber) and NPT-II− (amber) genes then was injected with approximately 10 copies per cell of *X. laevis* amber suppressor tRNA genes. Transformants expressing tk or NPT-II activity were selected on HAT or G418 medium respectively. Both cell types were obtained at a transformation frequency of approximately 10%. No transformants were obtained following injection of 5, 10 or 25 copies per cell of wild type *X. laevis* tyrosine tRNA genes.

A useful property of nonsense suppressors is that they can phenotypically correct, separate nonsense mutants in the same cell line. We found that G418 resistant cell lines obtained by injection *X. laevis* amber suppressor tRNA genes into the multiply marked cell lines, also express tk and gpt. Similarly cell lines selected for growth in HAT medium also expressed gpt and NPT-11 enzymatic activity. We also obtained transformants by injecting *X. laevis* suppressor tRNA genes into the multiply marked cell line and coselecting for tk+ and gpt+ phenotype (i.e. growth in medium containing thymidine, xanthine, mycophenolicacid and methotrexate).

We found that the growth rates of all four cell lines were similar. Thus the presence of functional suppressor tRNA genes in these mammalian cell lines did not markedly alter their growth rates. The three HAT$^r$ transformants selected for the tk+ phenotype (i.e. growth in HAT medium also exhibited gpt enzymatic activity (data not shown). Each of the above cell lines has been maintained in its respective selection medias (G418 or HAT) for over 70 generations without observable phenotypic change. Thus they can be considered stable cell lines when grown in their respective selection medium.

Equivalents

The procedure which we have just described for establishing mouse cell lines containing functional suppressor tRNA genes should be applicable to isolating similar lines in a wide spectrum of mammalian culture cells. Particularly useful for this purpose are the nonsense mutations in the Ecogpt and NPT-II genes which when suppressed confer a dominant selectable phenotype. Coreversion of multiple nonsense mutations may allow selection of endogenous suppressor genes, an alternative approach to the introduction of exogenously engineered suppressor genes. Either or both approaches should allow the generation of cell lines with suppressor genes of other codon specificity (e.g. ochre) or ones that suppress by insertion of other amino acids (e.g. serine, lysine, or tryptophan). Furthermore, by modulating the number of copies of the amber mutants and amber suppressor genes in a given transformant, it may be possible to create cell lines with different levels of suppressor activity.

Industrial Applications

Many tRNA genes are susceptible to conversion by site specific mutagenesis to a suppressor tRNA gene. By using our techniques a battery of suppressor tRNA genes capable of inserting a spectrum of amino acids at amber, ochre and opal mutations can be made available. The availability of cell lines containing such suppressor genes will make it possible to isolate many new viral mutants using simple host range screening procedures. The affected mutant gene product can often be identified since it is possible to readily distinguish between the mutant polypeptide fragment from the suppressed completed polypeptide chain. The stringency of nonsense mutations should facilitate complementation analysis. With these new genetic tools it should be possible to dissect the complex viral-host interactions leading to many viral induced diseases.

One specific industrial application is in the field of vaccine production. Animal viral vaccines are useful in protection against subsequent virus infections. The antigenic component of the vaccine is typically either inactivated virus particles or attenuated live virus. In the former case, virus particles are rendered inactive by a treatment that does not completely destroy their ability to stimulate a protecting immune response. In the latter case, virus variants that give non pathological infection of their natural host are selected by passage in different growth conditions. Vaccination with these variants stimulates a protective immune response without severe manifestation of disease. The use of nonsense mutants of virus as vaccines can combine some of the features of both types of conventional vaccines. Nonsense mutants should retain their complete antigenicity as particles and should yield attenuated infections of animals. The vaccine may also have higher efficacy and less disease manifestation. Viral mutants with one, two or more nonsense mutations can be isolated on permissive suppressor cell lines. Dominant selectable nonsense genes and suppressor genes can be used to create permissive suppressor cell lines. Host range growth of virus can be used to identify the appropriate mutants.

More generally, conditional expression of protein activity can be useful in many applications. For example, suppressor negative mammalian cells can be cultured that produce messenger RNA coding for a protein at such high levels that the protein would be lethal to the cell. When the gene specifying the messenger RNA contained a nonsense termination signal, the deleterious protein will not be efficiently synthesized and the cell colony will continue to grow. Just prior to harvest, expression of the protein at the high cell concentrations can be induced by switching on suppressor tRNA activity, resulting in high yields. The suppressor gene can be switched on or activated by changing the temperature of the cells or by chemical stimulation for examples.

We claim:

1. A method of suppressing a nonsense codon in a gene for production of a protein of interest in mammalian cells, the method comprising:
    (a) preparing an oligonucleotide primer comprising a region complementary to the nonsense codon;
    (b) preparing a DNA template for production of a tRNA molecule;
    (c) forming a suppressor gene from said template and primer by site specific mutagenesis; and
    (d) transforming the suppressor gene into a mammalian cell, whereby the nonsense codon will be suppressed.

2. The method of claim 1 wherein the nonsense codon is an amber (UAG) stop signal and the step of preparing a primer further comprises preparing a primer having a mismatched region (CUA) corresponding to the amber stop signal.

3. The method of claim 1 wherein the nonsense codon is an ochre (UAA) stop signal and the step of preparing a primer further comprises preparing a primer having a mismatched region (UUA) corresponding to the ochre stop signal.

4. The method of claim 1 wherein the nonsense codon is an op$^{41}$ (UGA) stop signal and the step of preparing a primer futher comprises preparing a primer having a mismatched region (UCA) corresponding to the opal stop signal.

5. The method of claim 1 wherein the step of preparing a DNA template further comprises preparing a template for the insertion of an amino acid chosen from the group consisting of tyrosine, serine, lysine, tryptophane, leucine, glutamine, glutamic acid, and glycine.

6. The method of claim 1 wherein the step of transforming the suppressor gene into a mammalian cell further comprises transforming the suppressor gene into a mammalian cell using a plasmid vector.

7. The method of claim 6 wherein the step of transforming the suppressor gene by plasmid vector further comprises using an SV40 vector.

8. A method of suppressing a frameshift mutation in a gene for production of a protein of interest in mammalian cells, the method comprising:
    (a) preparing an oligonucleotide primer comprising a region complementary to the frameshift mutation codon;
    (b) preparing a DNA template for production of a tRNA molecule;
    (c) forming a suppressor gene from said template and primer by site specific mutagenesis;
    (d) transforming the suppressor gene into a mammalian cell whereby the frameshift mutation will be suppressed.

9. The method of claim 8 wherein the frameshift mutation is a nucleotide deletion resulting in a shortened codon and the step of preparing a primer further comprises preparing a primer having a mismatched region corresponding to the shortened codon.

10. The method of claim 8 wherein the frameshift mutation codon is a nucleotide addition resulting in a lengthened codon and the step of preparing a primer further comprises preparing a primer having a mismatched region corresponding to the lengthened codon.

11. The method of claim 8 wherein the step of preparing a DNA template further comprises preparing a template for the insertion of an amino acid chosen from the group consisting of proline, glycine, lysine and threonine.

12. A method of transforming a suppressor gene into a mammalian cell, the method comprising:
   (a) preparing a selectable gene containing a nonsense codon the gene being capable of expressing a phenotype when the nonsense codon is suppressed;
   (b) introducing the selectable gene containing the nonsense codon into a plurality of mammalian cells;
   (c) introducing a suppressor gene formed by site-specific mutagenesis into the plurality of mammalian cells; and
   (d) selecting those cells which express the phenotype, thus indicating the transformation of the suppressor gene in the selected cells.

13. The method of claim 12 wherein the step of preparing a gene containing a selectable nonsense codon further comprises demonstrating the suppression of the nonsense codon in an organism chosen from the group consisting of bacteria and yeast prior to introducing the gene into mammalian cells.

14. The method of claim 12 wherein the step of introducing the gene containing the nonsense codon further comprises transfecting the mammalian cells with the gene.

15. The method of claim 12 wherein the step of introducing the gene containing the nonsense codon further comprises microinjecting the mammalian cells with the gene.

16. The method of claim 12 wherein the step of introducing the suppressor gene further comprises transfecting the mammalian cells with the gene.

17. The method of claim 12 wherein the step of introducing the suppressor gene further comprises microinjecting the mammalian cells with the gene.

18. The method of claim 1 further comprising:
   (e) mutating a virus against which a vaccine is sought, to incorporate into the genetic material of the virus at least one nonsense codon to disrupt viral replication;
   (f) growing the mutated virus in the transformed mammalian cell of step (d); and
   (g) harvesting the virus and producing a vaccine therefrom.

19. The method of claim 18 wherein the step of activating a suppressor gene further comprises adding an exogenous gene to the cells.

20. The method of claim 18 wherein the step of activating a suppressor gene further comprises altering the activity by changing the temperature of the cells.

21. The method of claim 1 further comprising:
   (e) mutating a gene for producing of the protein to incorporate at least one nonsense codon to prevent production of the complete protein;
   (f) transforming said mutated gene into a mammalian cell of step (d);
   (g) growing the gene-containing cell into a large population of cells; and
   (h) activating said suppressor gene capable of suppressing the nonsense mutation and thus permitting production of the complete protein.

* * * * *

UNITED STATES PATENT AND TRADEMARK OFFICE
CERTIFICATE OF CORRECTION

PATENT NO. : 4,687,737
DATED : August 18, 1987
INVENTOR(S) : Phillip A. Sharp et al It is certified that error appears in the above-identified patent and that said Letters Patent is hereby corrected as shown below:

On the title page inventors should read

--(75) Inventors: Phillip A. Sharp, Newton, Mass.;
Mario R. Capecchi; Salt Lake City, Utah;
Uttam L. RajBhandary , Lexington, Mass;
Frank A. Laski, Southfield, Mich; Robert M.
Hudziak, San Bruno, Calif.--.

Signed and Sealed this

Eighth Day of December, 1987

Attest:

DONALD J. QUIGG

*Attesting Officer*   *Commissioner of Patents and Trademarks*